United States Patent
Hess et al.

[11] Patent Number: 6,153,779
[45] Date of Patent: Nov. 28, 2000

[54] CU$^{II}$ AND ZN$^{II}$ PHENOXYL COMPLEXES AND RADICAL COMPLEXES THEREOF, METHODS FOR THEIR PREPARATION AND USE

[75] Inventors: Martina Hess, Mülheim; Phalguni Chaudhuri, Göttingen; Karl Wieghardt, Bochum, all of Germany

[73] Assignee: Degussa-Hüls Aktiengesellschaft, Frankfurt am Main, Germany

[21] Appl. No.: 09/340,410

[22] Filed: Jun. 28, 1999

[30] Foreign Application Priority Data

Jun. 26, 1998 [DE] Germany ............ 198 28 492
Jun. 2, 1999 [DE] Germany ............ 199 25 142

[51] Int. Cl.$^7$ ............ C07F 1/08; C07F 3/06
[52] U.S. Cl. ............ 556/113; 502/152; 556/135; 568/430; 568/431; 568/469; 568/472
[58] Field of Search ............ 556/113, 135; 502/152; 568/430, 431, 469, 472

[56] References Cited

PUBLICATIONS

Dul at al., Chemical Abstracts, vol. 108, No. 20, abstract No. 68561f (PL 136,898), May 1988.

(List continued on next page.)

*Primary Examiner*—Porfirio Nazario-Gonzalez
*Attorney, Agent, or Firm*—Smith Gambrell & Russell, LLP

[57] ABSTRACT

Quadridentate Cu$^{II}$ and Zn$^{II}$ phenoxyl complexes and phenoxyl radical complexes thereof, in which one ligand L is bonded to each metal atom and H$_2$L stands for the general formula

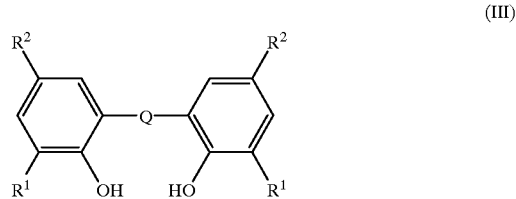

in which the bridge-unit Q stands for —S—, —O—, —N(R$^3$)—, —P(R$^4$)—, or ortho-NH—C$_6$H$_4$—NH— and R$^1$ and R$^2$ stand for radical-stabilizing residues.

Preferred radical complexes include

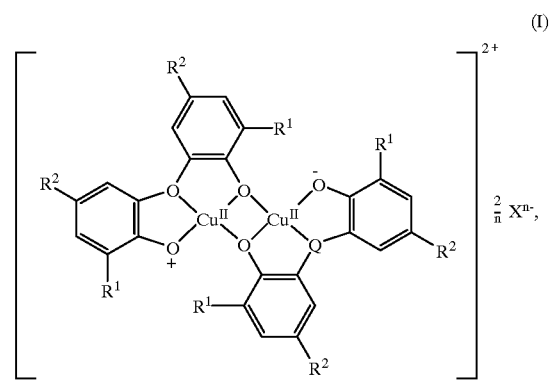

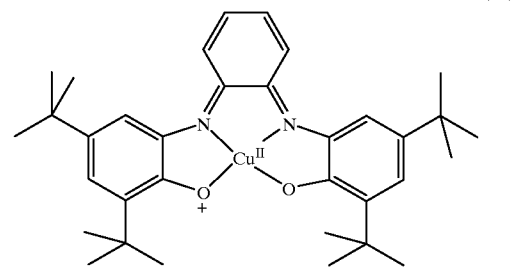

The radical complexes are oxidation catalysts for oxidizing organic substrates with O$_2$ in the course of which H$_2$O$_2$ is also formed.

19 Claims, 1 Drawing Sheet

OTHER PUBLICATIONS

Chemical & Engineering News, Jan. 26, 1998, S. 9, "Capturing an Enzyme's Essence", Sophie Wilkinson.

"Catalytic Galactose Oxidase Models: Biomimetic Cu(II) Phenoxyl–Radical Reactivity", Science, vol. 279, Jan. 23, 1988, Wang et al.

Key: 1    H release
       2    e transfer

CU<sup>II</sup> AND ZN<sup>II</sup> PHENOXYL COMPLEXES AND RADICAL COMPLEXES THEREOF, METHODS FOR THEIR PREPARATION AND USE

INTRODUCTION AND BACKGROUND

The subject matter of this invention relates to mononuclear $Cu^{II}$ and $Zn^{II}$ phenoxyl complexes and mono- and binuclear radical complexes thereof, methods for the preparation of the complexes and the use of the phenoxyl radical complexes as catalysts in oxidation reactions with oxygen, and in particular, for the oxidation of primary or secondary alcohols.

It is known that aldehydes can be produced by dehydrogenation or by oxidation of primary alcohols; in the first case, the by-product that forms is molecular hydrogen, in the second case, the by-product is water.

With the use of enzymatic redox systems, it is possible to oxidize different substrates, which leads to the formation of hydrogen peroxide as a coupling product. The oxidase which, as a rule, is flavin-dependent oxidizes the substrate, and the reduced form of the enzyme is reoxidized by molecular oxygen while forming hydrogen peroxide. For example, according to the German Patent No. DE-A 4,231,767, an enzyme with oxidase activity, such as glucose oxidase, in combination with the oxidizable substrate can be used as a bleaching system in bleaches and detergents. According to the U.S. Pat. No. 5,234,827, hydrogen peroxide can be produced in the aqueous phase, using a short-chain alcohol, an extracellular alcohol oxidase which is free from catalase activity. Drawbacks of the enzymatic systems for oxidation reactions and/or for the production of hydrogen peroxide are the restrictions with respect to the admissible pH and temperature range, the high substrate specificity which often limits the versatile use, and the risk of deactivating and thus reducing the activity of the enzyme as a result of an irreversible oxidation by means of the hydrogen peroxide that forms.

It is known that in its active form, galactose oxidase which catalyzes the oxidation of primary alcohols to form aldehydes and $H_2O_2$ contains a $Cu^{II}$ ion which is bonded to a tyrosyl radical that is S-modified in the ortho position. The galactose oxidase thus contains a radical cofactor—see, for example, N. Ito et al. in J. Mol. Biol. (1994), Vol. 238, p. 794, and R. M. Wachter et al. in J. Amer. Chem. Soc. (1996), Vol. 118, p. 2782. Using the structural models of $Cu^{II}$ phenoxyl for the active form of glucose oxidase as a starting point, Y. Wang, T. D. P. Stack et al. in Science (1998), Vol. 279, p. 537, introduced mononuclear $Cu^{II}$ compounds with quadridentate ligands which, under aerobic conditions, catalytically oxidize benzyl alcohols and allyl alcohols to form the corresponding aldehydes or ketones while at the same time forming hydrogen peroxide. According to an article in Chem. & Eng. News of Jan. 26, 1998, p.9, one of the specially active $Cu^{II}$ compounds, the preparation of which, however, is highly time- and cost-consuming, is a compound of the following formula:

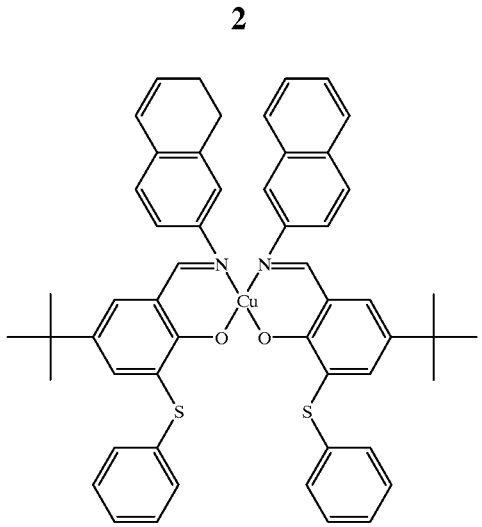

An object of the present invention is to identify additional $Cu^{II}$ phenoxyl complexes and $Cu^{II}$ phenoxyl radical complexes which can be obtained therefrom and which catalyze oxidation reactions with molecular oxygen. The new Cu phenoxyl radical complexes should be readily accessible.

Another object of the invention is to provide Cu phenoxyl radical complexes that make it possible to oxidize alcohols other than those so far oxidized with the previously known complexes.

A further object of this invention is to identify areas in which the substrate-catalyst systems can be used and in which the hydrogen peroxide that is formed in situ is purposefully utilized.

SUMMARY OF THE INVENTION

The above and other objects of this invention can be achieved by quadridentate $Cu^{II}$ or $Zn^{II}$ phenoxyl complexes and phenoxyl radical complexes thereof, in which each metal atom has one ligand L bonded to it and in which $H_2L$ stands for the formula:

(III)

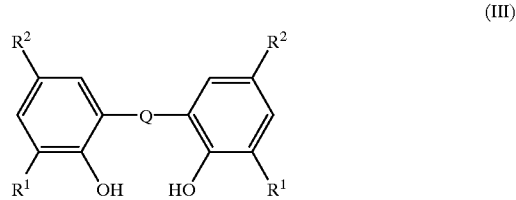

in which Q represents a bridge-unit selected from the group consisting of —S—, —O—, —N(R³)—, and —P(R⁴)— or for a bridge-unit of the formula ortho-NH—C₆H₄—NH—, $R^1$ and $R^2$ which may be identical to or different from each other represent radical-stabilizing residues, in particular alkyl with a tertiary C atom which is bonded to the phenolate ring, and $R^3$ and $R^4$ represent H or an alkyl group with 1–6 carbon atoms.

One of the $Cu^{II}$ phenoxyl radical complexes is binuclear and has the following formula I:

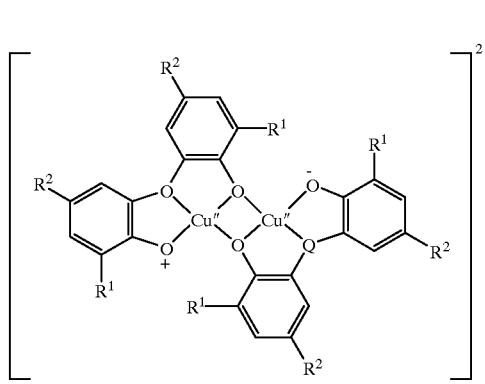

(I)

in which Q stands for a bridge-unit selected from the group consisting of —S—, —O—, —N(R³)—, and —P(R⁴)— and X stands for an anion with valence n and $R^1$, $R^2$, $R^3$, and $R^4$ have the meaning given above.

Complexes of formula I, in which bridge-unit Q is a thioether bridge, are preferred due to their greater stability to complexes with an ether bridge or an amine or phosphine bridge. $R^3$ and $R^4$ in the —N(R³)— and —P(R⁴)— bridge-unit can be hydrogen or a linear, branched, or cyclic alkyl group with 1–6 C atoms, for example, methyl, ethyl, n-propyl, isopropyl, n-butyl, sec-butyl, or cyclopentyl. The radical-stabilizing residues $R^1$ and $R^2$ occupy the ortho and para positions with respect to the phenolic oxygen atom. Linear and preferably branched alkyl groups, in particular those with a tertiary C atom that is bonded to the phenolate ring, such as tert-butyl, tert-amyl, and tert-hexyl, are well-known radical stabilizers. Thus, in addition, alkylthio and arylthio groups, such as i-propylthio and phenylthio, are also suitable as radical stabilizers and thus as $R^1$ and/or $R^2$. Anion X with valence n can be freely chosen, provided that it as such does not coordinate too strongly with the $Cu^{II}$ ion. X is preferably selected from the group comprising chloride, bromide, acetate, sulfite, and sulfate. Especially preferred binuclear $Cu^{II}$ phenoxyl radical complexes of formula I include those in which Q stands for a thioether bridge, $R^1$ and $R^2$ stand for tert-alkyl, in particular for tert-butyl, and X stands for chloride.

Binuclear $Cu^{II}$ phenoxyl radical complexes of formula I according to this invention can be obtained either by reacting a $Cu^I$ salt of the formula $Cu^I_nX$, wherein X and n have the meaning given above, with a tridentate phenolic ligand of formula III, wherein Q is, however, different from ortho-NH—$C_6H_4$—NH—, in the presence of an N-containing base B, in particular a tertiary amine, such as tri($C_1$–$C_4$) alkylamine, followed by a treatment with dry oxygen or a dry $O_2$-containing gas, or by treating the mononuclear $Cu^{II}$ phenoxyl complex of formula II, which forms as an intermediate product, with dry oxygen or an $O_2$-containing gas.

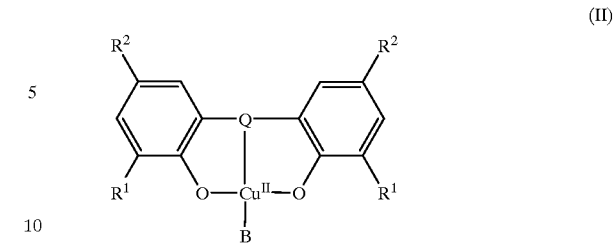

(II)

The $Cu^{II}$ phenoxyl complexes of formula II are paramagnetic whereas the $Cu^{II}$ phenoxyl radical complexes of formula I are diamagnetic. Because of the electron spectrum, the presence of phenoxyl radicals in formula I is guaranteed; the resonance Raman spectrum indicates a binuclear structure of formula I with two bridged phenolate ligands and two phenoxyl radicals.

In addition, mononuclear phenoxyl complexes of the formula $[M(L)]^0$ (Va) and mononuclear phenoxyl radical complexes thereof of the formulas $[M(L)]_n^+X^{n-}$ (Vb) and $[M(LH_2)]_n^+X^{n-}$ (Vc) were found, wherein M stands for $Cu^{II}$ or for $Zn^{II}$ and L stands for a quadridentate ligand, with $H_4L$ having the formula IV (corresponding to formula III, Q=ortho-NH—$C_6H_4$—NH—):

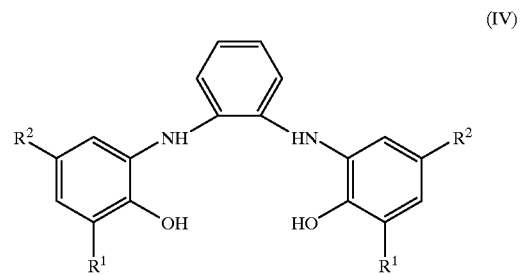

(IV)

In formula IV, $R^1$ and $R^2$ again represent radical-stabilizing groups (as in III). $R^1$=$R^2$=tert-butyl are especially preferred.

As an example, formula VI has the structure of a preferred neutral $Cu^{II}$ phenoxyl complex of type Va, with tert-butyl for $R^1$ and $R^2$.

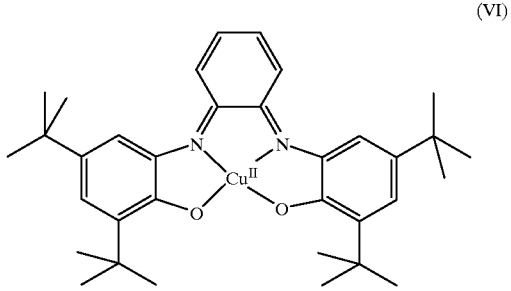

(VI)

The neutral $M^{II}$ phenoxyl complexes (Va) according to this invention can be obtained by reacting a $Cu^I$ salt or preferably complexes thereof or a $Zn^{II}$ salt with a phenolic compound of formula IV in the presence of a base, followed by a treatment with dry oxygen or a dry $O_2$-containing gas. Suitable Cu and Zn compounds include, for example, [$Cu^I$($CH_3CN$)$_4$]$ClO_4$, [$Cu^I$($NR_3$)$_4$]Cl and Zn($BF_4$)$_2$·$H_2O$, respectively, which can also be formed in situ.

The central o-phenylenediamine group in $H_4(L)$ (=IV) can be oxidized to form iminosemiquinone $H_3(L)$ and further to diiminoquinone $H_2(L)$; and the two phenolic groups can be oxidized to form H(L) and (L) by means of one-electron oxidization steps. As shown in the chart below which also lists the colors of the complexes, the five steps of oxidation of the quadridentate ligands are accessible in the corresponding $Cu^{II}$ and $Zn^{II}$ complexes:

| | M = $Cu^{II}$ | M = $Nz^{II}$ |
|---|---|---|
| $[M^{II}(L)]^{2+}$ | red | red |
| $-e\ ⇅\ +e$ | violet | green |
| $[M^{II}(L)]^{+}$ | green | blue |
| | blue | green |
| $-e\ ⇅\ +e$ | yellow | colorless |
| $[M^{II}(L)]^{0}$ | | |
| $-e\ ⇅\ +e$ | | |
| $[M^{II}(LH_2)]^{+}$ | | |
| $-e\ ⇅\ +e$ | | |
| $[M^{II}(LH_2)]^{0}$ | | |

The complexes mentioned above are formed, for example, from complexes of general formula $[M(L)]^0$ by electrochemical oxidation or reduction. Radical complexes with the cation $[M^{II}(L)]^+$ can also be obtained from $[M^{II}(L)]^0$ by oxidation, for example, with ferrocene hexafluorophosphate. Complexes with the cation $[M^{II}(L)]^1$ oxidize primary alcohols to aldehydes, and a phenoxyl radical complex with the cation of the formula $[M(LH_2)]^+$ is formed. Complexes of the $[M^{II}(LH_2)]^+$ type are oxidized with oxygen in an acid solution to form $[M^{II}(L)]^+$ while forming hydrogen peroxide.

To produce the $Cu^{II}$ phenoxyl complexes of formula II which, as intermediate products that can be readily isolated during the production of the $Cu^{II}$ phenoxyl radical complexes of formula I, as such are the subject matter of the invention, a $Cu^I$ salt and a tridentate phenolic ligand $LH_2$ of formula III, wherein Q is different from ortho-NH—$C_6H_4$—NH—, are reacted in the presence of a nitrogen-containing base B which acts as acid acceptor for the phenolic protons and also as a ligand in the complex of formula II, in a dry solvent, preferably in an inert gas atmosphere, and subsequently treated with a gas that contains $O_2$. Per equivalent of $Cu^I$, a minimum of 1 mol of $LH_2$ and a minimum of 3 equivalents of base are used. To produce especially preferred complexes of formula II, where Q is thio and $R^1$ and $R^2$ are tert-butyl, CuCl, 2,2'-thiobis(2,4-di-tert-butylphenol), and a trialkylamine in a molar ratio of 1 to equal to or greater than 1 to equal to or greater than 3, preferably 1:1:5, are used. Especially suitable solvents are methanol and open-chain or cyclic ethers.

Similarly, the quadridentate ligand $LH_4$ of formula IV and Cu or Zn salts can be used to produce neutral complexes that correspond to Va.

In the selection of the solvents for the production of the complexes, it is important to ensure that they do not coordinate with $Cu^{II}$ or $Zn^{II}$. The term "do not coordinate" is intended to mean that the tendency toward coordination is considerably less pronounced than that of the phenolate. Thus, because of its coordinating effect, acetonitrile, for example, is not a suitable solvent. Methanol and open-chain and cyclic ethers, on the other hand, are especially suitable solvents.

Among bases B, trialkylamines, such as trimethylamine, triethylamine, tri-n-propylamine, methyl diethylamine, dim-ethyl ethylamine, tri-n-butylamine, N-methylpiperidine, and N-methylmorpholine, and heterocyclic bases, such as pyridine, picoline, and N-methylpyrrole are suitable. The use of primary and secondary amines as the base is less recommended since, as will be shown below, these bases themselves can subsequently be oxidized by radicals of formula I. The reaction generally takes place at 20–100° C., and preferably at 40–60° C. The yellow solution obtained is subsequently treated with a controlled quantity of dry oxygen or an $O_2$-containing dry gas, such as air, preferably at 0–50° C., especially at 10–30° C.

During the production of II, the solution turns dark blue, and after being allowed to stand over a relatively long period of time, the complex of formula II precipitates in the form of blue crystals. With the ligand from $H_4(L)$ (=IV), it is similarly possible to obtain the phenoxyl complexes and phenoxyl radical complexes of $Cu^{II}$ and $Zn^{II}$. $[Cu^{II}(L)]^0$ (VI) forms green crystals, and the corresponding $[Zn^{II}(L)]^0$ complex forms anthracite-colored microcrystalline crystals.

The mononuclear $Cu^{II}$ phenoxyl complex of formula II can be transformed into the $Cu^{II}$ phenoxyl radical complex of formula I by dissolving II in a dry solvent, which does not coordinate with $Cu^{II}$, at a temperature range from preferably 0–50° C., especially at room temperature, and by allowing it to come into intensive contact with dry oxygen or with an oxygen-containing dry gas, as a result of which the blue solution takes on a dark green color and a green precipitate settles out.

According to another embodiment of this invention, it is possible to also obtain catalytically effective phenoxyl radical complexes directly from the $Cu^I$ or $Zn^{II}$ salt, the phenolic ligand III or IV, and a base B; in this case, following the reaction of the reaction participants (=Step i), a treatment with dry $O_2$ or an $O_2$-containing dry gas (=Step ii) is carried out at such an intensity level that the solution which first turns blue subsequently turns dark green. In this particular embodiment of the invention, per equivalent of $Cu^I$, a minimum of 1 mol of a phenolic ligand and a minimum of 2, preferably more than 2 equivalents of the base are used. Solvents to be preferred are linear and cyclic ethers. Although acetone is also a suitable solvent, problems, apparently as a result of the enolization, arise if, for example, cyclohexanone is used. Again, it is recommended that the reaction and the oxidation take place at the temperature conditions mentioned earlier.

It was discovered that in dry THF, to which excess ethanol is added at 20° C. under an inert gas atmosphere (argon), an $O_2$-free green solution of a $Cu^{II}$ phenoxyl radical complex of formula I turns blue and that one equivalent of acetaldehyde is formed.

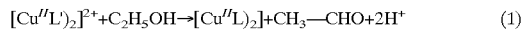

$$[Cu''L')_2]^{2+}+C_2H_5OH\rightarrow[Cu''L)_2]+CH_3—CHO+2H^+ \quad (1)$$

By exposing the blue solution to molecular oxygen, a dark green solution is again obtained within a few minutes, and the radical complex is reconverted while one equivalent of hydrogen peroxide forms.

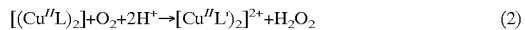

$$[(Cu''L)_2]+O_2+2H^+\rightarrow[Cu''L')_2]^{2+}+H_2O_2 \quad (2)$$

In principle, the combination of equations (1) and (2) leads to the homogeneously catalyzed oxidation of ethanol to form acetaldehyde with $O_2$ while $H_2O_2$ is formed. Similarly, in the presence of I, other primary alcohols, with the exception of methanol, can be converted into the corresponding aldehydes as well. The by-products that form as a result of a C—C coupling that proceeds according to a different reaction mechanism are symmetrical vicinal diols and secondary products thereof, i.e., a-hydroxy ketones and a-diketones. Secondary alcohols lead to ketones and/or symmetrical vicinal diols and possibly their secondary products mentioned above. At this time, it is not yet known which parameters of the primary and secondary alcohol that is to be oxidized are responsible for the conversion into the corresponding aldehyde or ketone and which are responsible for the conversion into a symmetrical vicinal diol. While the main product of the oxidation of isopropanol is pinacol, 2-butanol is nearly quantitatively oxidized to 2-butanone. On application of a $Cu^{II}$ phenoxyl radical complex of formula I according to this invention which is either added or formed in situ in the reaction medium, it is possible to oxidize primary or secondary aliphatic, cycloaliphatic, aromatic aliphatic and olefinic unsaturated alcohols or alcohols containing other substituents.

Similarly, it is possible to also oxidize and secondary amines by using the catalyst of formula I according to this invention or its precursor II: From primary amines, imines and the hydrolysis products thereof, i.e., aldehydes or ketones, are obtained. From secondary amines, Schiff bases are obtained. Again, as a result of an oxidation with C—C coupling, primary and secondary amines are also able to form symmetrical vicinal diamines or secondary products thereof, such as a-ketones. In each case, those skilled in the art will determine in a preliminary test which product is the main product and what the overall product spectrum looks like.

The mononuclear phenoxyl radical complexes of formula $[M^{II}(L)]^+X^-$ (Vb) which can be obtained by oxidation of the neutral phenoxyl complexes $[M^{II}(L)]$ (Va) or in situ from a metal compound and a compound $LH_4$ according to formula IV also are especially suitable as oxidation catalysts to oxidize primary alcohols with air to obtain aldehydes while hydrogen peroxide forms. With this catalyst system, secondary alcohols are practically not oxidized at all.

BRIEF DESCRIPTION OF INVENTION

The accompanying drawing illustrates a cyclic process according to the invention.

DETAILED DESCRIPTION OF INVENTION

Figure 1:
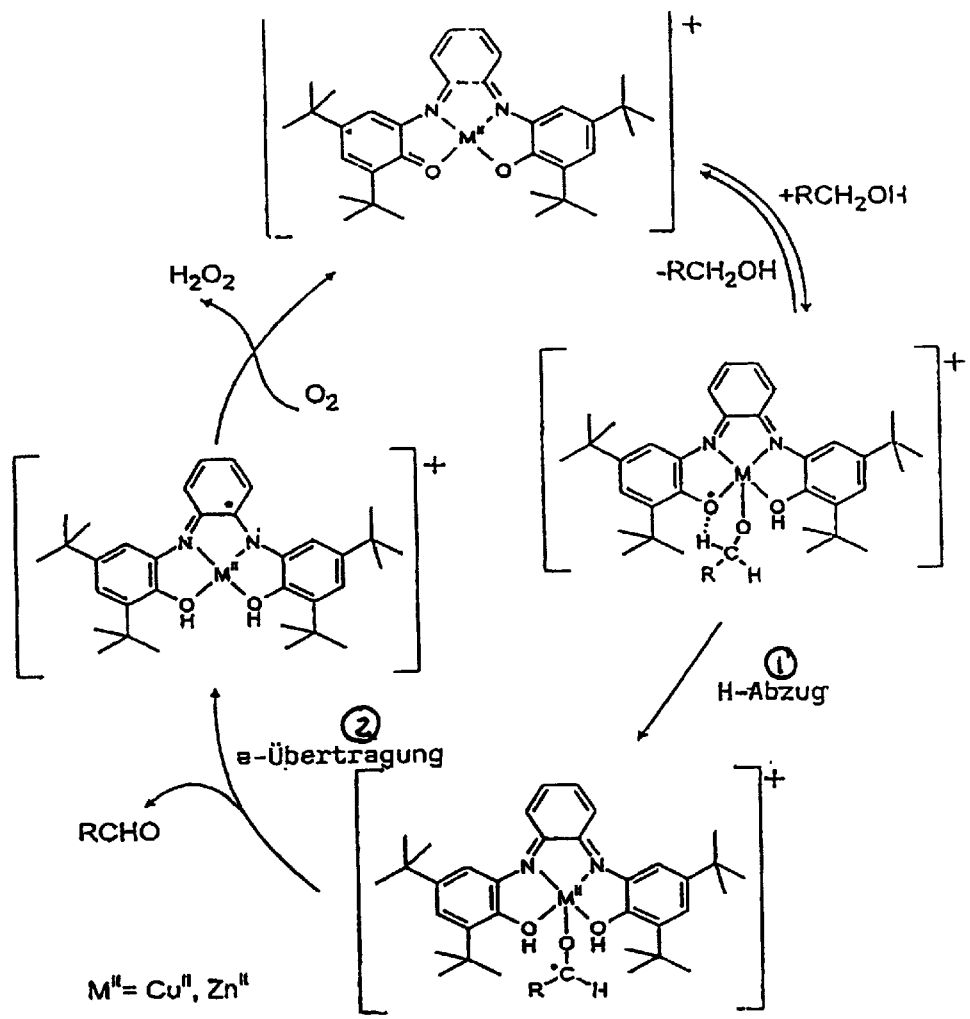

According to a preferred embodiment of the oxidation of alcoholic or aminic substrates, these substrates are added to a solution, for example, to an ether, which contains a catalytic quantity of the $Cu^{II}$ phenoxyl radical complex of formula I or a precursor thereof and stirred while air or $O_2$ is introduced. It is recommended that the molar ratio of substrate to catalyst be in a range from 10–10,000, especially from 100–1,000. The oxidation product of the substrate and the $H_2O_2$ can be separated by means of an extractive process, after which they can be processed. Similarly, primary alcohols can be oxidized by adding a mononuclear $Cu^{II}$ or $Zn^{II}$ phenoxyl radical complex $[M(L)]^+$ $X^-$ (Vb) according to this invention or by allowing such a complex to be formed in situ.

Phenoxyl radical catalysts according to this invention can also be used in combination with an alcoholic substrate in such a way that the hydrogen peroxide, which forms in the substrate-catalyst system as a result of oxidation with air, is used for bleaching, cleaning, and disinfecting purposes. In this case, the substrates used are, for example, sugar, naturally occurring sugar alcohols, and naturally occurring hydroxycarboxylic acids, such as lactic acid and tartaric acid. The hydrogen peroxide that forms can oxidize pigments and thus decolorize them.

The oxidation reaction of primary and secondary alcohols or amines which is catalyzed according to this invention generally does not lead beyond the steps of the carbonyl or imine compounds mentioned. Thus, primary alcohols are not converted into carboxylic acids. Compared to other oxidation reactions, this is particularly beneficial. Another advantage is that the oxidation proceeds substantially under neutral and very mild conditions, thus making it possible to oxidize even alcohols with substituents that are sensitive to acids or bases or with structures that are sensitive to heat. Thus, the oxidation reaction can also be suitably used to oxidize native substances as well as compounds with protective groups which are sensitive to acids or bases.

It is, for example, possible to convert retinol into retinal which is obtained in a high yield and glycerol into glyceraldehyde, with the glycerol being oxidized in the ketalized form. The hydrogen peroxide that is formed on application according to this invention can be readily obtained using inexpensive substrates and can be used for bleaching, cleaning, and disinfecting purposes.

EXAMPLE 1

Preparation of the complex of formula II with Q=—S—, $R^1=R^2$=tert-butyl, B=triethylamine Ligand $LH_2$ of formula III was prepared as described by S. Pastor et al., J. Heterocycl. Chem. (1984), Vol. 21, p.1285. A suspension of CuCl (0.10 g; 1.0 mmol), $LH_2$ (0.44 g; 1.0 mmol), and $NEt_3$ (0.5 mL) in dry $O_2$-free $CH_3OH$ (50 mL) was refluxed for 1 h in an inert Ar atmosphere. The clear yellow solution which was cooled to 20° C. was stirred while being exposed to air, after which the solution turned dark blue. After 2 days, blue microcrystals of the complex mentioned of formula II precipitated. The recrystallization from $CH_3OH$/n-pentane (2:1 vol) results in blue rhombic crystals. Yield: 0.48 g; 80%.

EXAMPLE 2

Preparation of the complex of formula I with Q=—S—, $R^1=R^2$=tert-butyl, X=Cl

A suspension of CuCl, $LH_2$, $NEt_3$ (quantities identical to those listed in Example 1) in dry THF was refluxed for 30 min in an Ar atmosphere. While stirring, dry pure oxygen was passed for 1 h through the clear yellow solution which was cooled to 20° C. (the exclusion of $H_2O$ is essential). The solution first turns blue and then dark green, and subsequently a microcrystalline green precipitate of the radical complex of formula I according to this invention settles out. Recrystallization from dry THF. Yield: 0.12 g; 11%.

EXAMPLES 3–9

Oxidation of primary and secondary alcohols and primary amines in the presence of a binuclear phenoxyl radical complex (I)

$1.25 \times 10^{-5}$ of mol CuCl and ligand $LH_2$ (with Q=S and $R^1=R^2$=tert-butyl) each and $2.5 \times 10^{-5}$ of mol triethylamine were dissolved in dry THF (50 mL) in an inert Ar atmosphere at 50° C. Subsequently, $6.25 \times 10^{-3}$ mol of alcohol were added and stirred for 12 h at 20° C. while exposing it to air. The reaction mixture was analyzed by gas chromatography; after complexing with titanyl sulfate in aqueous $H_2SO_4$, the $H_2O_2$ was determined by means of spectrophotometry. The substrates and the products obtained are listed in the table below.

Benzyl amine and aminoethanol were similarly oxidized. The results are listed in the table below.

TABLE

| Example No. | Substrate | Products (% yield relative to the alcohol) | |
|---|---|---|---|
| 3 | Ethanol | Acetaldehyde | (63) |
| | | Butane-2,3-diol | (1.5) |
| | | 3-Hydroxy-butanone-2 | (1.5) |
| | | Butane-2,3-dione | (4) |
| | | $H_2O_2$ | (70) |
| 4 | Benzyl alcohol | Benzaldehyde | (60) |
| | | 1,2-Diphenyl ethanediol | (1) |
| | | Benzoin | (1) |
| | | Benzil | (3) |
| | | $H_2O_2$ | (65) |
| 5 | Isopropanol | Acetone | (2) |
| | | Pinacol | (61) |
| | | $H_2O_2$ | (61) |
| 6 | Diphenyl carbinol | Tetraphenyl ethanediol | (68) |
| | | $H_2O_2$ | (66) |
| 7 | Isobutanol | Butan-2-one | (70) |
| | | $H_2O_2$ | (70) |
| 8 | Benzylamine | Benzaldehyde | (~20%) |
| | | $H_2O_2$ | (~20%) (Not optimized) |
| 9 | Aminoethanol | Glyoxal | (Quantitative) |
| | | $H_2O_2$ | |

EXAMPLES 10–15

In situ formation of the catalyst, wherein Q stands for —NH and $R^1$ and $R^2$ stand for tert-butyl, and oxidation of alcohols To 50 mL each of a THF solution containing $2.5 \times 10^{-4}$ mol/L CuCl and NH ligand (2,2'-aminobis(2,4-di-tert-butyl phenol) each and $(2.5–25)10^{-4}$ mol/L triethylamine, 6.25 mmol of substrate were added, and the mixture was stirred while exposing it to air. The reaction mixtures were analyzed. The substrates and results are listed in the table below.

TABLE

| | | Yield | |
|---|---|---|---|
| Example No. | Substrate | Aldehyde (%) | H2O2 % |
| 10 | Ethanol | Acetaldehyde | (68) |
| 11 | Benzyl alcohol | Benzaldehyde | (74) |
| 12 | 1-Hexanol | 1-Hexanol | (52) |
| 13 | Isopropanol | No oxidation | |
| 14 | 2-Butanol | No oxidation | |
| 15 | Cyclohexanol | No oxidation | |

With the catalyst that does not contain an amine bridge, it is possible to readily oxidize primary alcohols but not secondary alcohols.

Under conditions identical to those in Example 1, except that the aminic ligand mentioned above is used, the corresponding complex of formula II, wherein Q=—NH—, was produced. The analysis of the complex as well as the analysis of the crystal structure indicate that the product obtained is the mononuclear neutral complex of formula II.

EXAMPLE 16

Preparation of NN'-bis(3,5-di-tert-butyl-2-hydroxyphenyl)-1,2-phenylenedia mine (=ligand $H_4L$ of formula IV)

A suspension of 3,5-di-tert-butyl catechol (8.88 g; 40 mmol), o-phenylenediamine (2.1 g; 20 mmol), and triethylamine (0.4 mL) in n-heptane (120 mL) was stirred for 4 days while being exposed to air. The beige precipitate was isolated and washed with pentane. Yield: 4.6 g; 45%.

EXAMPLE 17

Preparation of the Cu complex $[Cu^{II}(L)]^0$ according to formula VI

A solution of $[Cu(CH_3CN)_4]$ $(ClO_4)$ (1 mmol; 0.327 g), $H_4L$ (=IV) according to Example 14 (1 mmol), and triethylamine (0.5 mL) in dry $O_2$-free methanol (50 mL) was refluxed for 0.5 h in an inert Ar atmosphere. The yellow solution which was cooled to 20° C. was exposed to air, as a result of which the solution turned dark green. After 2 h, green microcrystals of the complex of formula (V) precipitated. The recrystallization from acetonitrile leads to green crystals. Yield: 0.28 g; 49%.

EXAMPLE 18

Preparation of the Zn complex $[Zn^{II}(L)]^0$ (as in VI)

A solution of $Zn(BF_4)^2 \cdot 2$ $H_2O$ (1 mmol; 0. 24 g), $H_4L$ (=IV) according to Example 14 (1 mmol; 0. 516 g), and $NEt_3$ (0.5 mL) in dry methanol (50 mL) was heated for 0.5 h in an argon atmosphere. The yellow solution which was cooled to room temperature was exposed to air. The solution turned dark green, and within one day, an anthracite-colored microcrystalline complex precipitated. Yield: 0.32 g; 62%.

EXAMPLE 19

Oxidation of methanol 0.25 mmol each of CuCl and ligand $H_4L$ (=IV) and triethylamine (10 μL) were stirred for 10 min in dry THF (50 mL) in an inert Ar atmosphere. Subsequently, 253 μL of absolute methanol were added, and the mixture was stirred for 24 h at 20° C. while exposing it to air. The reaction mixture was analyzed by means of gas chromatography; after complexing with titanyl sulfate, the $H_2O_2$ was determined by means of spectrophotometry. Products: formaldehyde 60%/23 h; $H_2O_2$ 65%/23 h.

EXAMPLE 20

Preparation of complex $[M^{II}(LH_2)]^0$, wherein $M=Cu^{II}$ or $Zn^{II}$ (as in Vc)

In an $O_2$-free methanolic solution, $Zn(ClO_4)_2 \cdot 6H_2O$ or $Cu(ClO_4) \cdot 6H_2O$ is reacted in the presence of a tertiary amine in an inert Ar atmosphere. The complex settles out in the form of, respectively, a yellowish brown or brown precipitate.

EXAMPLE 21

Preparation of complex $[M^{II}(L)]PF_6$, wherein $M=Cu^{II}$ or $Zn^{II}$ (as in Vb)

A solution of the complex of Example 15 or 16 in $CH_2Cl_2$ was allowed to react with ferrocene hexafluorophosphate at $-10°$ C., after which it crystallized out at $-20°$ C. (Cu complex) and $-80°$ C. (Zn complex), respectively. The Cu complex settles out in the form of a violet precipitate, the Zn complex in the form of a green precipitate.

Further variations and modifications of the invention will be apparent to those skilled in the art from the foregoing and are intended to be encompassed by the claims appended hereto. German priority applications 198 28 492.6 and 199 25 142.8 are relied on and incorporated herein by reference.

What is claimed is:

1. A $Cu^{II}$ or $Zn^{II}$ phenoxyl complex or a phenoxyl radical complex thereof, comprising a ligand L bonded to a copper or zinc atom, wherein $H_2L$ corresponds to formula III as follows:

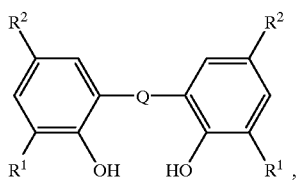

(III)

wherein Q represents a bridge-unit selected from the group consisting of —S—,

—O—, —N(R³)—, and —P(R⁴)—, or a bridge-unit of formula: ortho-NH—C₆H₄—NH—;

R¹ and R², which may be identical to or different from one another, represent a radical-stabilizing residue;

R³ represents a hydrogen or an alkyl group with 1 to 6 carbon atoms; and

R⁴ represents a hydrogen or an alkyl group with 1 to 6 carbon atoms;

wherein the complex is binuclear when Q represents —S—, —O—, —N(R³)—, or —P(R⁴)—, and the complex is mononuclear when Q represents ortho-NH—C₆H₄—NH—.

2. The complex according to claim 1, wherein at least one of the radical-stabilizing residues R¹ and R² is an alkyl group having a tertiary carbon atom bonded to the phenolate ring.

3. The complex according to claim 1, wherein R¹ and R² each represent tert-butyl.

4. A process for producing a complex according to claim 1, comprising:

(i) reacting a metal salt or a metal complex of copper or zinc with the compound of formula III, wherein a minimum of one mole of ligand per gram-atomic weight of metal is present, this reacting step taking place in a dry O₂-free solvent, in the presence of at least two gram equivalents of a nitrogen-containing base per gram-atomic weight of metal, at 20 to 100° C., in an inert gas atmosphere to form a solution, and (ii) contacting the solution obtained in step (i) with dry oxygen or an O₂ containing dry gas.

5. The process according to claim 4, comprising a further step of (iii) separating any settled out precipitate.

6. A process for oxidizing an organic substrate from primary or secondary alcohols and amines, comprising reacting a substrate, in the presence of a catalyst, with O₂ or an O₂-containing dry gas in a dry solvent, with the formation of hydrogen peroxide, wherein the catalyst comprises the complex according to claim 1.

7. The process according to claim 6, wherein the catalyst is formed in situ.

8. The Cu^{II} or Zn^{II} phenoxyl complex or phenoxyl radical complex according to claim 1, wherein the complex is binuclear and corresponds to formula I as follows:

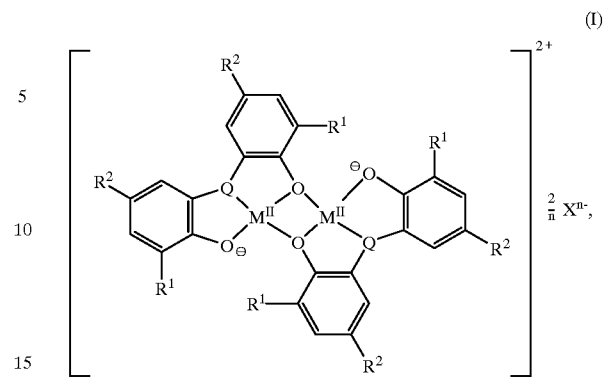

(I)

wherein Q represents a bridge-unit selected from the group consisting of —S—, —O—, —N(R³)—, and —P(R⁴)—;

M represents a metal selected from the group consisting of copper and zinc;

X represents an anion having a valance n; and n represents the valance of the anion.

9. The complex according to claim 8, wherein at least one of the radical-stabilizing residues R¹ and R² is an alkyl having a tertiary carbon atom bonded to the phenolate ring.

10. The complex according to claim 8, wherein R¹ and R² each represent tert-butyl.

11. The complex according to claim 8, wherein Q is a thioether group and X is a chloride anion.

12. The complex according to claim 8, wherein Q is a thioether group and X is a chloride anion.

13. The complex according to claim 10, wherein Q is a thioether group and X is a chloride anion.

14. A process for producing the complex according to claim 8, comprising:

(i) reacting a metal salt or a metal complex of copper or zinc with a compound of formula III as follows:

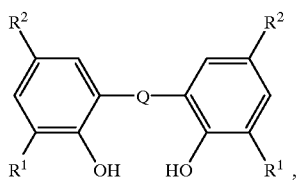

(III)

wherein a minimum of one mole of the compound of formula III is present per gram-atomic weight of metal, wherein this reacting step takes place in a dry O₂-free solvent, in the presence of at least two gram equivalents of a nitrogen-containing base per gram-atomic weight of metal, at 20 to 100° C., in an inert gas atmosphere to form a solution, and (ii) contacting the solution obtained in step (i) with dry oxygen or an O₂ containing dry gas.

15. The process according to claim 14, comprising a further step of (iii) separating any settled out precipitate.

16. A process for oxidizing an organic substrate from primary or secondary alcohols and amines with oxygen comprising: reacting a substrate, in the presence of a catalyst, with $O_2$ or an $O_2$-containing dry gas in a dry solvent, wherein the catalyst is a complex as claimed in claim 8.

17. The process according to claim 16, wherein the catalyst is formed in situ.

18. The $Cu^{II}$ or $Zn^{II}$ phenoxyl complex or phenoxyl radical complex according to claim 1, having a formula selected from the group consisting of $[M(L)]^0$, $[M(L)]_n^+X^{n-}$ and $[M(LH_2)]_n^+X^{n-}$, wherein M stands for copper or zinc and L stands for a ligand, with $H_4(L)$ having the formula IV as follows:

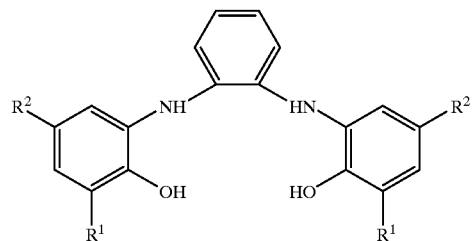

(IV)

X represents an anion having a valance n; and
n represents the valence of the anion.

19. The $Cu^{II}$ or $Zn^{II}$ phenoxyl complex or phenoxyl radical complex according to claim 18, wherein $R^1$ and $R^2$ each represent tert-butyl.

* * * * *